Figure 1:
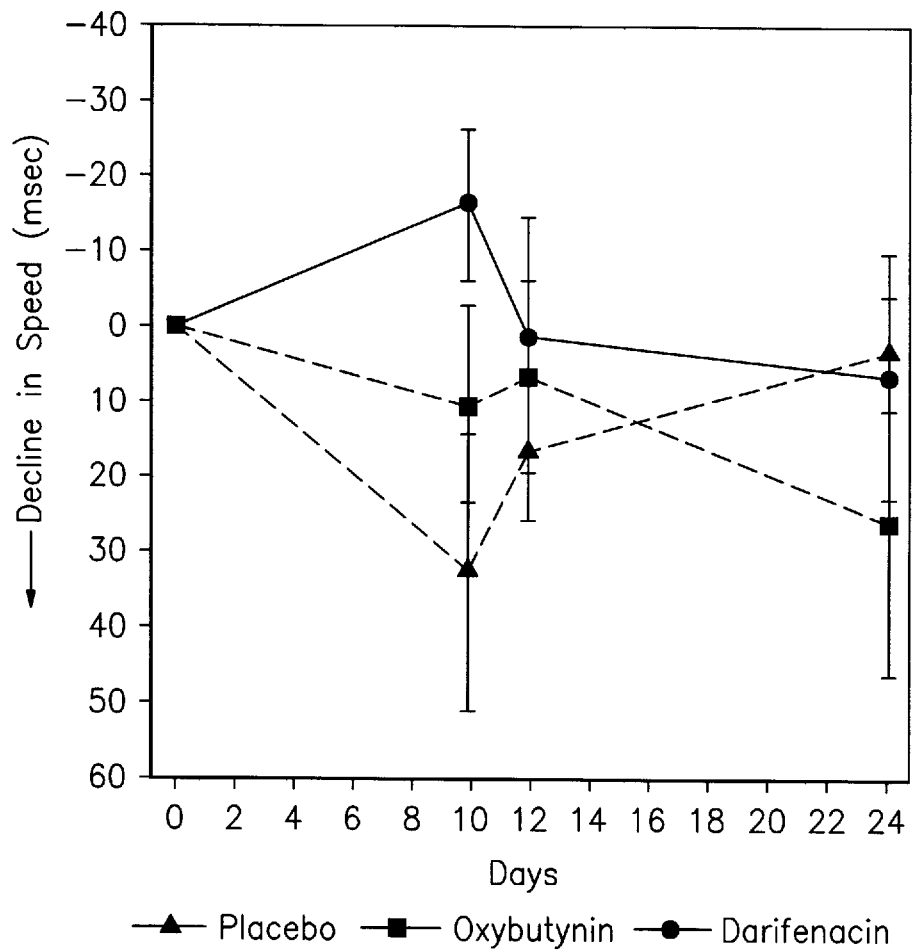

United States Patent [19]
Allen et al.

[11] Patent Number: 5,837,724
[45] Date of Patent: Nov. 17, 1998

[54] METHOD OF ENHANCING COGNITION

[75] Inventors: Michael John Allen, Sandwich, United Kingdom; Brian Frank Johnson, Groton, Conn.; Brian Robert Leaker; Robert Michael Wallis, both of Sandwich, United Kingdom

[73] Assignee: Pfizer Inc., New York, N.Y.

[21] Appl. No.: 872,891

[22] Filed: Jun. 11, 1997

[30] Foreign Application Priority Data

Jun. 18, 1996 [GB] United Kingdom .................... 9612710

[51] Int. Cl.⁶ ...................................................... A61K 31/40
[52] U.S. Cl. ............................................................. 514/422
[58] Field of Search ............................................. 514/422

[56] References Cited

U.S. PATENT DOCUMENTS 5,233,053  8/1993  Cross et al. .............................. 548/568

OTHER PUBLICATIONS

F–D–C Reports, The Pink Sheet, vol. 57, Issue 44, Oct. 1995.

Derwent Abstract of WO 9709980 Nichols et al., Aug. 1996.

Primary Examiner—Raymond Henley, III
Attorney, Agent, or Firm—Peter C. Richardson; Gregg C. Benson; A. Dean Olson

[57] ABSTRACT

Darifenacin, and its pharmaceutically acceptable salts, are useful in the treatment of cognitive impairment. The invention also discloses the use of combinations of darifenacin, or a pharmaceutically acceptable salt thereof, with an acetylcholinesterase inhibitor, in the treatment of cognitive impairment.

8 Claims, 1 Drawing Sheet

METHOD OF ENHANCING COGNITION

This application is based on Great Britain application serial no. 9612710.5 filed on Jun. 18, 1996.

This invention relates to a new use of darifenacin and its pharmaceutically acceptable salts.

Darifenacin is (S)-2-{1-[2-(2,3-dihydrobenzofuran-5-yl)ethyl]-3-pyrrolidinyl}-2,2-diphenyl-acetamide and is disclosed in European Patent No 0388054, Examples 1B and 8, and is referred to therein as 3-(S)-(-)-(1-carbamoyl-1,1-diphenylmethyl)-1-[2-(2,3-dihydro-benzofuran-5-yl)ethyl]pyrrolidine. It is indicated in the treatment of urinary incontinence and irritable bowel syndrome and has the following structure:

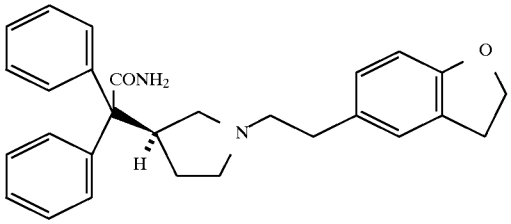

It has now been found that darifenacin, and its pharmaceutically acceptable salts, is able to enhance cognition. It is therefore indicated in the treatment of cognitive impairment, and as a cognition enhancer in persons not suffering from cognitive impairment.

Thus, according to the present invention, there is provided the use of darifenacin, or a pharmaceutically acceptable salt thereof, in the manufacture of a medicament for the treatment of cognitive impairment.

Causes of cognitive impairment which may be mentioned are Alzheimer's disease and age-related memory disorder.

The invention further provides a method of enhancing cognition in a person not suffering from cognitive impairment, which comprises administering an effective amount of darifenacin, or a pharmaceutically acceptable salt thereof, to that person.

The invention further provides a method of treatment of cognitive impairment, which comprises administering a therapeutically effective amount of darifenacin, or a pharmaceutically acceptable salt thereof, to a patient in need of such treatment.

In the present indication, a suitable dosage of darifenacin, or a pharmaceutically acceptable salt thereof, for a 70 kg person, is in the range 3.75–40 mg daily, for example 7.5–30 mg daily. The dosage may be administered in, say, 3 divided doses or in a single controlled release formulation (such as described in International Patent Application N° PCT/EP96/03719). Conventional dosage forms and modes of administration are described in EP 0388054.

European Patent N° 0296560 discloses a number of compounds indicated as acetylcholinesterase inhibitors useful in the treatment of Alzheimer's disease. The compound of claim 3 and Example 4 (1-benzyl-4-[(5,6-dimethoxy-1-indanon)-2-yl]methylpiperidine, also known as donepizil, E-2020 and ARICEPT™) is of particular interest. Suitable doses of the compounds are indicated to be in the range 0.1 to 300 mg, preferably 1 to 100 mg, per adult per day.

The use of an acetylcholinesterase inhibitor (preferably donepizil or a pharmaceutically acceptable salt thereof) in combination with darifenacin, or a pharmaceutically acceptable salt thereof, may be particularly beneficial, and may give rise to a synergistic effect.

Therefore, the invention further provides a pharmaceutical formulation comprising darifenacin, or a pharmaceutically acceptable salt thereof, and an acetylcholinesterase inhibitor, together with a pharmaceutically acceptable adjuvant, diluent or carrier.

The invention also provides pharmaceutical products containing darifenacin, or a pharmaceutically acceptable salt thereof, and an acetylcholinesterase inhibitor, as a combined preparation for simultaneous, separate or sequential use in the treatment of cognitive impairment.

The invention also provides a method of treatment of cognitive impairment, as described above, which further comprises administering a therapeutically effective amount of an acetylcholinesterase inhibitor.

EXAMPLE

Comparison of the effects of darifenacin and oxybutynin upon cognitive function in the elderly A. Methods Study design Thirty six elderly (65 +years) subjects with urge incontinence were planned to complete this single centre, double blind, placebo controlled, parallel group out-patient study. Patients received one of three treatment conditions: placebo; darifenacin (in the form of its hydrobromide salt, 5 mg tid) or oxybutynin (10 mg daily; 2.5 mg in the morning and afternoon and 5 mg in evening). The final dose was given on the morning of day 12 and this was double the usual morning dose (i.e. 10 mg darifenacin or 5 mg oxybutynin).

CDR testing schedule a. Training

Training on the CDR system took place prior to the first day of the trial in order to familiarise the volunteers with the procedure and overcome the initial learning variability. Four training sessions were planned for each volunteer, two being conducted during the screening period and two on another day prior to day 0.

b. Study days

The CDR assessments were completed on days 0, 10, 12 and on the post study follow-up. On days 10 and 12 the assessments were conducted 45–60 minutes after the morning or afternoon dose, with all assessments being conducted at approximately the same time of day.

Cognitive assessments

The CDR Computerised Cognitive Assessment System

A selection of tasks from the CDR computerised cognitive assessment system was administered, parallel forms of the tests being presented on each testing session. All tasks were computer-controlled, the information being presented on high resolution monitors, and the response recorded via response modules containing two buttons, one marked 'NO' and the other 'YES'. The tests administered included the following:

Choice Reaction Time: Either the word 'NO' or the word 'YES' was presented on the monitor and the volunteer was instructed to press the corresponding button as quickly as possible. There were 30 trials for each of which the stimulus word is chosen randomly with equal probability and there is a varying inter-stimulus interval.

Statistics

Summary statistics were computed for each assessment by dose condition. For each measure and for each volunteer the assessment conducted prior to the first dose on day 0 was then used as a baseline and subtracted from all subsequent data to compute 'change from day 0' scores. Summary statistics were also computed for these data by dose condition. The latter data were plotted to give a visual representation of the data.

The data were subjected to an ANOVA with main effects of treatment group (COND) and study data (DAY). The treatment groups were compared using the LSMEANS statement: darifenacin and oxybutynin were separately compared with placebo and the two active treatments were also compared.

B. Results

Data Collected 24 patients completed the study. Seven of these patients were randomised to receive darifenacin, eight to receive oxybutynin and nine placebo. In addition, two patients (numbers 2 and 39) completed up to the day 10 assessment. Both these patients were randomised to receive darifenacin. Their data were not included in the main analysis.

The data for the Choice Reaction Time test is illustrated in FIG. 1.

C. Conclusion

Darifenacin made a statistically significant improvement in cognitive function as measured by the Choice Reaction Time test. This result was consistent with an earlier study involving young volunteers.

We claim:

1. A pharmaceutical formulation comprising darifenacin, or a pharmaceutically acceptable salt thereof, and an acetylcholinesterase inhibitor, together with a pharmaceutically acceptable adjuvant, diluent or carrier.

2. A formulation as claimed in claim 1, wherein the acetylcholinesterase inhibitor is donepizil, or a pharmaceutically acceptable salt thereof.

3. A method of enhancing cognition in a person not suffering from cognitive impairment, which comprises administering an effective amount of darifenacin, or a pharmaceutically acceptable salt thereof, to that person.

4. A method of treatment of cognitive impairment, which comprises administering a therapeutically effective amount of darifenacin, or a pharmaceutically acceptable salt thereof, to a patient in need of such treatment.

5. A method as claimed in claim 4, wherein the cognitive impairment results from Alzheimer's disease.

6. A method as claimed in claim 5, wherein the cognitive impairment results from age-related memory disorder.

7. A method as claimed in claim 4 which further comprises administration of a therapeutically effective amount of an acetylcholinesterace inhibitor.

8. A method as claimed in claim 7, wherein the acetylcholinesterase inhibitor is donepizil, or a pharmaceutically acceptable salt thereof.

* * * * *